United States Patent
Eastham et al.

(10) Patent No.: US 7,265,240 B2
(45) Date of Patent: Sep. 4, 2007

(54) PROCESS FOR THE CARBONYLATION OF ETHYLENICALLY UNSATURATED COMPOUNDS

(75) Inventors: Graham R. Eastham, Durham (GB); Cristina Jimenez, Fife (GB); David Cole-Hamilton, Fife (GB)

(73) Assignee: Lucite International UK Limited, Hampshire (GB)

( * ) Notice: Subject to any disclaimer, the term of this patent is extended or adjusted under 35 U.S.C. 154(b) by 0 days.

(21) Appl. No.: 10/524,034

(22) PCT Filed: Aug. 4, 2003

(86) PCT No.: PCT/GB03/03383

§ 371 (c)(1),
(2), (4) Date: Oct. 11, 2005

(87) PCT Pub. No.: WO2004/014834

PCT Pub. Date: Feb. 19, 2004

(65) Prior Publication Data

US 2006/0122435 A1    Jun. 8, 2006

(30) Foreign Application Priority Data

Aug. 10, 2002    (GB) .................... 02186138

(51) Int. Cl.
- C07C 67/36    (2006.01)
- C07C 51/12    (2006.01)
- C07C 51/14    (2006.01)
- C07C 51/16    (2006.01)

(52) U.S. Cl. ............ 560/175; 562/519; 562/522; 562/523

(58) Field of Classification Search ............ None
See application file for complete search history.

(56) References Cited

U.S. PATENT DOCUMENTS

| | | | |
|---|---|---|---|
| 4,786,443 A | 11/1988 | Drent et al. |
| 4,960,926 A | 10/1990 | Drent |
| 5,004,604 A | 4/1991 | Terness et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,258,546 A | 11/1993 | Klusener et al. |
| 6,103,927 A | 8/2000 | De Castro Loureiro Barreto Rosa et al. |
| 6,156,934 A | 12/2000 | Suykerbuyk et al. |
| 6,348,621 B1 | 2/2002 | Wang et al. |
| 6,706,912 B2 | 3/2004 | Drent et al. |
| 6,743,911 B2 | 6/2004 | Drent et al. |

FOREIGN PATENT DOCUMENTS

| | | |
|---|---|---|
| EP | 0 055 875 | 7/1982 |
| EP | 0 106 379 | 4/1984 |
| EP | 0 235 864 | 9/1987 |
| EP | 0495 548 | 9/1995 |
| WO | WO96/19434 | 6/1996 |
| WO | WO 01/68583 | 9/2001 |
| WO | WO 01/72697 | 10/2001 |

OTHER PUBLICATIONS

"Handbook of Chemistry and Physics," 76th Ed., Lide, David R., et al., C.R.C. Press, 1995.
"Homogeneous Transition Metal Catalysis—A Gentle Art," MASTERS, C., Chapman and Hall, 1981.

Primary Examiner—Sikarl A. Witherspoon
(74) Attorney, Agent, or Firm—Venable LLP; Marina V. Schneller

(57) ABSTRACT

A process for the carbonylation of ethylenically unsaturated compounds is described. The process comprises reacting an ethylenically unsaturated compound with carbon monoxide in the presence of a source of hydroxyl groups and a catalyst system. The catalyst system is obtained by combining: (a) metal of Group VIII or a compound thereof; and (b) a bidentate phosphine of general formula (I) The carbonylation reaction is carried out at a temperature of between −30° C. to 49° C. and under a CO partial pressure of less than $30 \times 10^5$ N.m$^{-2}$

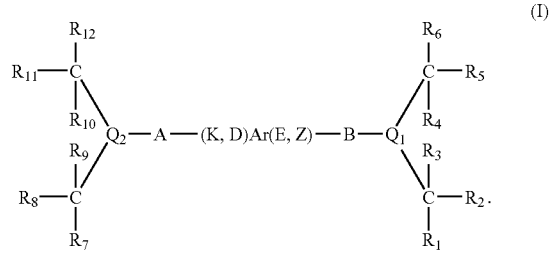

(I)

33 Claims, No Drawings

PROCESS FOR THE CARBONYLATION OF ETHYLENICALLY UNSATURATED COMPOUNDS

The invention relates to the carbonylation of ethylenically unsaturated compounds by reaction with carbon monoxide in the presence of a catalyst system.

The carbonylation of ethylenically unsaturated compounds using carbon monoxide in the presence of an alcohol or water and a catalyst system comprising a group VIII metal, example, palladium, and a phosphine ligand, example an alkyl phosphine, cycloalkyl phosphine, aryl phosphine, pyridyl phosphine or bidentate phosphine, has been described in numerous European patents and patent applications, example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved.

The main problem with the previously disclosed catalyst systems is that, although relatively high reaction rates can be achieved, the palladium catalyst dies off quickly which is industrially unattractive.

It has been disclosed in WO96/19434 that a particular group of bidentate phosphine compounds can provide remarkably stable catalysts which require little or no replenishment; that use of such bidentate catalysts leads to reaction rates which are significantly higher than those previously disclosed; that little or no impurities are produced at high conversions.

In addition, WO 96/19434 discloses that the same catalyst process when used with respect to propene has been found to be more difficult.

WO 01/68583 discloses rates for the same process used for higher alkenes of C3 or more carbon atoms when in the presence of an externally added aprotic solvent. WO 96/19434 utilises reaction conditions in the examples of $30 \times 10^5$ N.m$^{-2}$ and 100° C. Similarly, WO 01/68583 discloses 30 and 60 bar carbon monoxide and also 100° C. The most preferred range for temperature in WO 96/19434 is from 70-120° C. and the most preferred pressure in the same document is from $5 \times 10^5$ to $50 \times 10^5$ N.m$^{-2}$. Similarly, in WO 01/68583 the most preferred temperature range is that of 80-120° C., whereas the most preferred partial pressure is in the range of 5 to 65 bar.

Surprisingly, it has been found that improved selectivity and improved linearity of final product can be found under conditions of lower temperature and lower carbon monoxide pressure than taught by the prior art. Still more surprisingly, an aprotic solvent is not required to achieve this as taught by WO 01/68583.

According to a first aspect of the present invention there is provided a process for the carbonylation of ethylenically unsaturated compounds which process comprises reacting said ethylenically unsaturated compound with carbon monoxide in the presence of a source of hydroxyl groups and of a catalyst system, the catalyst system obtainable by combining:
(a) a metal of Group VIII or a compound thereof: and
(b) a bidentate phosphine of general formula (I)

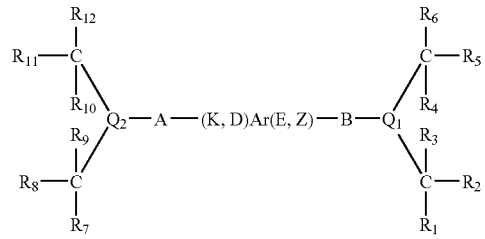

wherein:
Ar is a bridging group comprising an optionally substituted aryl moiety to which the phosphorus atoms are linked on available adjacent carbon atoms;
A and B each independently represent lower alkylene;
K, D, E and Z are substituents of the aryl moiety (Ar) and each independently represent hydrogen, lower alkyl, aryl, Het, halo, cyano, nitro, OR$^{19}$, OC(O)R$^{20}$, C(O)R$^{21}$, C(O)OR$^{22}$, NR$^{23}$R$^{24}$, C(O)NR$^{25}$R$^{26}$, C(S)R$^{25}$R$^{26}$, SR$^{27}$, C(O)SR$^{27}$, or -J-Q$^3$(CR$^{13}$(R$^{14}$)(R$^{15}$))CR$^{16}$(R$^{17}$)(R$^{18}$) where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, OR$^{19}$, OC(O)R$^{20}$, C(O)R$^{21}$, C(O)OR$^{22}$, NR$^{23}$R$^{24}$, C(O)NR$^{25}$R$^{26}$, C(S)R$^{25}$R$^{26}$, SR$^{27}$ or C(O)SR$^{27}$;
R$^1$ to R$^{18}$ each independently represent lower alkyl aryl, or Het;
R$^{19}$ to R$^{27}$ each independently represent hydrogen, lower alkyl, aryl or Het;
Q$^1$, Q$^2$ and Q$^3$ (when present) each independently represent phosphorous, arsenic or antimony and in the latter two cases references to phosphine or phosphorous above are amended accordingly;
wherein the carbonylation reaction is carried out at a temperature of between −30° C. to 49° C. and under a CO partial pressure of less than $30 \times 10^5$ N.m$^2$.

Such a process is referred to hereinafter as "the process of the invention".

Preferably, when K, D, E or Z represent -J-Q$^3$(CR$^{13}$(R$^{14}$)(R$^{15}$))CR$^{16}$(R$^{17}$)(R$^{18}$), the respective K, D, E or Z is on the aryl carbon adjacent the aryl carbon to which A or B is connected or, if not so adjacent, is adjacent a remaining K, D, E or Z group which itself represents -J-Q$^3$(CR$^{13}$(R$^{14}$)(R$^{15}$))CR$^{16}$(R$^{17}$)(R$^{18}$).

Suitably, the process of the invention may be used to catalyse the carbonylation of an ethylenically unsaturated compound in the presence of carbon monoxide and a hydroxyl group containing compound i.e. the process of the invention may catalyse the conversion of an ethylenically unsaturated compound to the corresponding carboxylic acid or ester, respectively, depending on the choice of hydroxyl group containing compound used. Conveniently, the process of the invention may utilise highly stable compounds under typical carbonylation reaction conditions such that they require little or no replenishment. Conveniently, the process of the invention may have an increased rate of the carbonylation reaction of an ethylenically unsaturated compound compared to known processes. Conveniently, the process of the invention may promote high conversion rates of the ethylenically unsaturated compound, thereby yielding the desired product in high yield with little or no impurities.

Consequently, the commercial viability of a carbonylation process, such as the carbonylation of an ethylenically unsaturated compound, may be increased by employing the process of the invention.

The term "Ar" or "aryl" when used herein, includes six-to-ten-membered carbocyclic aromatic groups, such as phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined below).

The term "Het", when used herein, includes four-to-twelve-membered, preferably four-to-ten-membered ring systems, which rings contain one or more heteroatoms selected from nitrogen, oxygen, sulfur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{19}$, $OC(O)R^{20}$, $C(O)R^{21}$, $C(O)OR^{21}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulfur atoms, or by silano or dialkylsilcon groups.

Lower alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulfur atoms, or by silano or dialkylsilicon groups, and/or be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het wherein $R^{19}$ to $R^{27}$ each independently represent hydrogen, aryl or lower alkyl.

Similarly, the term "lower alkylene" which A, B and J (when present) represent in a compound of formula I, when used herein, includes $C_1$ to $C_{10}$ groups which can be bonded at two places on the group and is otherwise defined in the same way as "lower alkyl".

Halo groups with which the above-mentioned groups may be substituted or terminated include fluoro, chloro, bromo and iodo.

Where a compound of the formula (I) contains an alkenyl group, cis (E) and trans (Z) isomerism may also occur. The present invention includes the individual stereoisomers of the compounds of formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula I(b) may function as ligands that coordinate with the Group VIIIB metal or compound thereof (a) to form the compounds for use in the invention. Typically, the Group VIIIB metal or compound thereof (a) coordinates to the one or more phosphorous, arsenic and/or antimony atoms of the compound of formula I.

Preferably, $R^1$ to $R^{16}$ each independently represent lower alkyl or aryl. More preferably, $R^1$ to $R^{18}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^{16}$ each independently represent $C_1$ to $C_6$ alkyl, which is optionally substituted as defined herein. Most preferably, $R^1$ to $R^{18}$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^1$ to $R^3$, $R^4$ to $R^6$, $R^7$ to $R^9$, $R^{10}$ to $R^{12}$, $R^{13}$ to $R^{15}$ or $R^{16}$ to $R^{18}$ together independently may form cyclic structures such as 1-norbornyl or 1-norbornadienyl. Alternatively, one or more of the groups may represent a solid phase to which the ligand is attached.

In a particularly preferred embodiment of the present invention $R^1$, $R^4$, $R^7$, $R^{10}$, $R^{13}$ and $R^{16}$ each represent the same lower alkyl, aryl or Het moiety as defined herein, $R^2$, $R^5$, $R^6$, $R^{11}$, $R^{14}$ and $R^{17}$ each represent the same lower alkyl, aryl or Het moiety as defined herein, and $R^3$, $R^6$, $R^9$, $R^{12}$, $R^{15}$ and $R^{18}$ each represent the same lower alkyl, aryl or Het moiety as defined herein. More preferably $R^1$, $R^4$, $R^7$, $R^{10}$, $R^{13}$ and $R^{16}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$, $R^{11}$, $R^{14}$ and $R^{17}$ each independently represent the same $C_1$-$C_6$ alkyl as defined above; and $R^3$, $R^6$, $R^9$, $R^{12}$, $R^{15}$ and $R^{18}$ each independently represent the same $C_1$-$C_6$ alkyl as defined above. For example: $R^2$, $R^4$, $R^7$, $R^{10}$, $R^{13}$ and $R^{16}$ each represent methyl; $R^2$, $R^5$, $R^8$, $R^{11}$, $R^{14}$ and $R^{17}$ each represent ethyl; and, $R^3$, $R^6$, $R^9$, $R^{12}$, $R^{15}$ and $R^{18}$ each represent n-butyl or n-pentyl.

In an especially preferred embodiment of the present invention each $R^1$ to $R^{18}$ group represents the same lower alkyl, aryl, or Het moiety as defined herein. Preferably, each $R^1$ to $R^{18}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably, each $R^1$ to $R^{18}$ represents methyl.

In the compound of formula I, preferably each $Q^1$, $Q^2$ and $Q^3$ (when present) are the same. Most preferably, each $Q^1$, $Q^2$ and $Q^3$ (when present) represents phosphorous.

Preferably, in the compound of formula I, A, B and J (when present) each independently represent $C_1$ to $C_6$ alkylene which is optionally substituted as defined herein, for example with lower alkyl groups. Preferably, the lower alkylene groups which A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—.

Preferably, in the compound of formula I when K, D, E or Z does not represent -J-$Q^3(CR^{13}(R^{14})(R^{15}))CR^{16}(R^{17})(R^{18})$, K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E or Z represents hydrogen.

Preferably, in the compound of formula I when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula I when K, D, E or Z does not represent -J-$Q^3(CR^{13}(R^{14})(R^{15}))CR^{16}(R^{17})(R^{18})$ and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1$-$C_6$ alkyl (more particularly unsubstituted $C_1$-$C_6$ alkyl), especially hydrogen.

Preferably, in the compound of formula I when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula I include those wherein:
A and B each independently represent unsubstituted $C_1$ to $C_6$ alkylene;
K, D, Z and E each independently represent hydrogen, $C_1$-$C_6$ alkyl, phenyl, $C_1$-$C_6$ alkylphenyl or J-$Q^3(CR^{13}(R^{14})(R^{15}))CR^{16}(R^{17})(R^{18})$ where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.
$R^1$ to $R^{18}$ each independently represent $C_1$ to $C_6$ alkyl, phenyl or $C_1$ to $C_6$ alkylphenyl.

Further preferred compounds of formula I include those wherein:
A and B both represent —$CH_2$— or $C_2H_4$, particularly $CH_2$;
K, D, Z and E each independently represent hydrogen, $C_1$-$C_6$ alkyl phenyl or $C_1$-$C_6$ alkyl or -J-$Q^3(CR^{13}(R^{14})(R^{15}))CR^{16}(R^{17})(R^{18})$ where J is the same as A; or two of K, D, E and Z together with the carbon atoms of the aryl ring to which they are attached form an unsubstituted phenyl ring;
$R^1$ to $R^{18}$ each independently represent $C_1$ to $C_6$ alkyl;

Still further preferred compounds of formula I include those wherein:
$R^1$ to $R^{18}$ are the same and each represents $C_1$ to $C_6$ alkyl, particularly methyl.

Still further preferred compounds of formula I include those wherein:
K, D, Z and E are each independently selected from the group consisting of hydrogen or $C_1$ to $C_6$ alkyl, particularly where each of K, D, Z and E represent the same group, especially where each of K, D, Z and E represent hydrogen; or
K represents —$CH_2$-$Q^3(CR^{13}(R^{14})(R^{15}))CR^{16}(R^{17})(R^{18})$ and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula I include those wherein:

each $R^1$ to $R^{12}$ is the same and represents methyl;
A and B are the same and represent —$CH_2$—;
K, D, Z and E are the same and represent hydrogen.

The present invention provides a process for the carbonylation of an ethylenically unsaturated compound comprising contacting an ethylenically unsaturated compound with carbon monoxide and a hydroxyl group containing compound in the presence of a catalyst compound as defined in the present invention.

Suitably, the hydroxyl group containing compound includes water or an organic molecule having a hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol.

The amount of alcohol is not critical. Generally, amounts are used in excess of the amount of ethylenically unsaturated compound to be carbonylated. Thus the alcohol may serve as the reaction solvent as well, although, if desired, separate solvents may also be used.

It will be appreciated that the end product of the reaction is determined at least in part by the source of hydroxyl group containing compound used. If water is used as the hydroxyl group containing compound then the end product is the corresponding carboxylic acid, whereas use of an alkanol produces the corresponding ester.

Suitably, the ethylenically unsaturated compound may include more than one carbon-carbon double bond, wherein the double bonds are conjugated or non-conjugated.

Preferably, the ethylenically unsaturated compound has 1 to 3 carbon-carbon double bonds per molecule, particularly only 1 or 2 carbon-carbon double bonds per molecule, generally only 1 carbon-carbon double bond per molecule.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compound to hydroxyl group containing compound may vary between wide limits and suitably lies in the range of 1:0.1 to 1:10, preferably from between 2:1 to 1:2 up to a large excess of hydroxyl group containing compounds when the latter is also the reaction solvent.

The amount of the catalyst of the invention used in the carbonylation process of the ethylenically unsaturated compound is not critical. Good results may be obtained when, preferably, the amount of Group VIII metal is in the range $10^{-7}$ to $10^{-1}$ moles per mole of ethylenically unsaturated compound, more preferably, $10^{-6}$ to $10^{-2}$ moles, most preferably $10^{-5}$ to $10^{-2}$ moles per mole of ethylenically unsaturated compound. Preferably, the amount of bidentate compound of formula I to unsaturated compound is in the range $10^{-7}$ to $10^{-1}$, more preferably, $10^{-6}$ to $10^{-2}$, most preferably, $10^{-5}$ to $10^{-2}$ moles per mole of ethylenically unsaturated compound.

Suitably, although non-essential to the invention, the carbonylation of an ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane (diglyme), diethylether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds eg. benzene, toluene, ethyl benzene o-xylene, m-xylene, p-xylene, chlorobenzene, o-dichlorobenzene, m-dichlorobenzene; alkanes, including halo variants of such compounds eg. hexane, heptane, 2,2,3-trimethylpentane, methylene chloride and carbon tetrachloride; nitriles eg. benzonitrile and acetonitrile.

Very suitable are aprotic solvents having a dielectric constant that is below a value of 50, more preferably in the range of 3 to 8, at 298.15 K and $1\times10^5$ $Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1\times10^5$ $Nm^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

If the hydroxyl group containing compound is an alkanol, an aprotic solvent will be generated by the reaction as the ester carbonylation product of the ethylenically unsaturated compound, carbon monoxide and the alkanol is an aprotic solvent.

The process may advantageously be carried out in an excess of aprotic solvent, i.e. at a ratio (v/v) of aprotic solvent to hydroxyl group containing compound of at least 1:1. Preferably, this ratio ranges from 1:1 to 10:1 and more preferably from 1:1 to 5:1. Most preferably the ratio (v/v) ranges from 1.5:1 to 3:1.

Despite the aforegoing it is preferred that the reaction is carried out in the absence of any external aprotic solvent ie. an aprotic solvent not generated by the reaction itself.

The catalyst compounds of the present invention may act as a "heterogeneous" catalyst or a "homogeneous" catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 μm.

More preferably, the surface area is in the range of from 50 to 500 m²/g, the pore volume is in the range of from 0.5 to 2.5 cc/g and the average particle size is in the range of from 20 to 200 μm. Most desirably the surface area is in the range of from 100 to 400 m²/g, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I, for example a substituent K, D, Z and E of the aryl moiety, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depend upon the nature of the substituents(s) of the compound and the groups of the support. For example, reagents such as carbodiimides, 1,1'-carbonyldiimidazole, and processes such as the use of mixed anhydrides, reductive animation may be employed.

According to a further aspect, the present invention provides the use of process of the invention wherein the catalyst is attached to a support.

Particularly preferred is when the organic groups $R^1$, $R^2$, $R^3$, $R^4$, $R^5$, $R^6$, $R^7$, $R^8$, $R^9$, $R^{10}$, $R^{11}$ and $R^{12}$ when associated with their respective carbon atom form composite groups which are at least as sterically hindering as t-butyl. Steric hindrance in this context is as discussed at page 14 et seq of "Homogenous Transition Metal Catalysis—A Gentle Art", by C Masters, published by Chapman and Hall 1981.

These steric groups may be cyclic, part-cyclic or acyclic. When cyclic or part cyclic, the group may be substituted or unsubstituted or be saturated or unsaturated. The cyclic or part cyclic groups may contain, including the tertiary carbon atom, from $C_4$-$C_{30}$, more preferably $C_6$-$C_{20}$, most preferably $C_{10}$-$C_{15}$ carbon atoms in the cyclic structure. The cyclic structure may be substituted by one or more substituents selected from halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^{18}$, $C(S)NR^{16}R^{17}$, aryl or Het, wherein $R^{10}$ to $R^{18}$ each independently represent hydrogen, aryl or lower alkyl, and/or be interrupted by one or more oxygen or sulphur atoms, or by silano or dialkylsilcon groups.

The bridging group Ar is an aryl moiety, eg. a phenyl group, which may be optionally substituted, provided that the two phosphorus atoms are linked to adjacent carbon atoms, eg. at the 1 and 2 positions on the phenyl group. Furthermore, the aryl moiety may be a fused polycyclic group eg. naphthalene, biphenylene or indene.

Examples of suitable bidentate ligands are bis(di-t-butyl phosphino)-o-xylene (also known as 1,2bis(di-t-butylphosphinomethyl)benzene); 1,2bis(diadamantylphosphinomethyl)benzene; 1,2bis(diadamantylphosphinomethyl)naphthalene; 1,2bis(di-t-pentylphosphino)-o-xylene (also known as 1,2bis(di-t-pentyl-phosphinomethyl)benzene); and bis2,3 (di-t-butyl phosphinomethyl) naphthalene. Additionally, the bidentate phosphine may be bonded to a suitable polymeric substrate via at least one of the bridging group Ar, the linking group A or the linking group B eg. bis (di-t-butyl phosphino)-o-xylene may be bonded via the xylene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group VIII metal present is from 1 to 50 eg. 1 to 10 and particularly from 1 to 5 mol per mol of metal. More preferably, the mol:mol range of compounds of formula I to Group VIIIB metal is in the range of 1:1, to 3:1, most preferably in the range of 1:1 to 1.25:1. Conveniently, the possibility of applying these low molar ratios is advantageous, as it avoids the use of an excess of the compound of formula I and hence minimises the consumption of these usually expensive compounds. Suitably, the catalysts of the invention are prepared in a separate step preceding their use in-situ in the carbonylation reaction of an ethylenically unsaturated compound.

Conveniently, the process of the invention may be carried out by dissolving the Group VIIIB metal or compound thereof as defined herein in a suitable solvent such as one of the hydroxyl group containing compounds or aprotic solvents previously described (a particularly preferred solvent would be the ester or acid product of the specific carbonylation reaction eg. Methylnonanoate for octene carbonylation) and subsequently admixing with a compound of formula I as defined herein.

The carbon monoxide may be used in the presence of other gases which are inert in the reaction. Examples of such gases include hydrogen, nitrogen, carbon dioxide and the noble gases such as argon.

Suitable Group VIIIB metals or a compound thereof which may be combined with a compound of formula I include cobalt, nickel, palladium, rhodium and platinum. Preferably, the Group VIIIB metal is palladium or a compound thereof. Suitable compounds of such Group VIII metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zerovalent palladium complexes particularly those with labile ligands, e.g.

triphenylphosphine or alkenes such as dibenzylideneacetone or styrene OR tri(dibenzylideneacetone)dipalladium may be used.

The anion may be derived from or introduced as one or more of an acid having a pKa measured in aqueous solution at 18° C. of less than 4, more preferably, less than 3, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts, other than unsubstituted carboxylates, listed supra.

The quantity of anion present is not critical to the catalytic behaviour of the catalyst system. The molar ratio of anion to palladium may be from 1:1 to 500:1, preferably from 2:1 to 100:1 and particularly from 3:1 to 30:1. Where the anion is provided by a combination of acid and salt, the relative proportion of the acid and salt is not critical. As mentioned, the catalyst system of the present invention may be used homogeneously or heterogeneously. Preferably, the catalyst system is used homogeneously.

The catalyst system of the present invention is preferably constituted in the liquid phase which may be formed by one or more of the reactants or by the use of a suitable solvent.

The molar ratio of the amount of ethylenically unsaturated compound used in the reaction to the amount of hydroxyl providing compound is not critical and may vary between wide limits, eg. from 0.001:1 to 100:1 mol/mol.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity and linearity. A further advantage is that the other components which contain the catalyst system which may be recycled and/or reused in further reactions with minimal supplementation of fresh catalyst.

Preferably, the carbonylation is carried out at a temperature of between −10 to 45° C., more preferably 0° C. to 40° C., most preferably 5° C. to 35° C. An especially preferred temperature is one chosen between 20° C. to 30° C. Advantageously, the carbonylation can be carried out at moderate temperatures, it is particularly advantageous to be able to carry out the reaction at room temperature.

Preferably, the carbonylation is carried out at a CO partial pressure of less than $15 \times 10^5$ N.m$^{-2}$, more preferably less than $5 \times 10^5$ N.m$^2$. Especially preferred is atmospheric pressure or $0.80$-$1.20 \times 10^5$ N.m$^2$, The reaction may be carried out on any ethylenically unsaturated compound including ethylene although there is no linearity advantage as such with ethylene. Preferably, the reaction is therefore suitable for $C_3$-$C_{20}$ compounds, more preferably, $C_3$-$C_{18}$, most preferably $C_3$-$C_{12}$ compounds. The invention should be particularly advantageous for longer alkenes such as $C_4$-$C_{20}$, more preferably $C_4$-$C_{18}$, most preferably, $C_4$-$C_{12}$ compounds.

The process may be carried out on ethylenically unsaturated compounds having 2 or more carbon atoms such as $C_2$-$C_{20}$ atoms or $C_3$-$C_{20}$ atoms or $C_4$-$C_{20}$ atoms. The alternative upper range of carbon atoms in such compounds may be taken as $C_{18}$ or $C_{15}$ or $C_{12}$ in increasing order of preference. The alternative lower range of carbon atoms in any of the aforesaid ranges of ethylenically unsaturated compounds may be $C_4$, $C_5$, or $C_6$ in increasing order of preference. The ethylenically unsaturated compound is, preferably, an alkene having 1, 2 or 3 or more carbon-carbon double bonds per molecule.

Any such alkene can be substituted or non-substituted. Suitable substituents include $C_{1-8}$ alkyl and $C_{1-22}$ aryl groups. Unless otherwise specified, the ethylenically unsaturated compound may, when there are sufficient number of carbon atoms, be linear or branched, be substituted, be cyclic, acyclic or part cyclic/acyclic, and/or be optionally substituted or terminated by one or more substituents selected from lower alkyl, aryl, alkylaryl, Het, halo, $OR^{19}$, $OC(O)R^{20}$, $C(O)R^{21}$, $C(O)OR^{22}$, $NR^{23}R^{24}$, $C(O)NR^{25}R^{26}$, CN, $SR^{27}$ wherein $R^{19}$ to $R^{27}$ each independently represent hydrogen or lower alkyl. Olefins thus substituted include styrene and alkyl esters of unsaturated carboxylic acids, such as methacrylate. Suitably, the ethylenically unsaturated compound may exhibit cis (E) and trans (Z) isomerism.

Examples of suitable ethylenically unsaturated compounds may be independently selected from ethene, propene, 1-butene, 2-butene, isobutene, 1-pentene, 2-pentene, 3-pentene and branched isomers thereof, 1-hexene and its isomers, 1-heptene and its isomers, 1-octene and its isomers, 1-nonene and its isomers, 1-decene and its isomers, the $C_{11}$-$C_{20}$ alkenes and their known isomers, 3-pentenenitrile, methyl-3-penteneoate, 1,3 butadiene, 1,3-pentadiene, 1,3 hexadiene, 1,3 cyclohexadiene, 2,4-leptadiene, 2-methyl 1,3 butadiene.

The use of stabilising compounds with the catalyst system may also be beneficial in improving recovery of metal which has been lost from the catalyst system. When the catalyst system is utilized in a liquid reaction medium such stabilizing compounds may assist recovery of the group VI or VIIIB metal.

Preferably, therefore, the catalyst system includes in a liquid reaction medium a polymeric dispersant dissolved in a liquid carrier, said polymeric dispersant being capable of stabilising a colloidal suspension of particles of the group VI or VIIIB metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group VI or VIIIB metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group VI or VIIIB metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group VI or VIIIB metal or metal compound.

By substantially stabilise is meant that the precipitation of the group VI or VIIIB metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid).

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinyipyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group VI or VIIIB metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably between 1:1 and 200.1. Preferably, the polymer:metal mass ratio in g/g is up to 1000, more preferably, up to 400, most preferably, up to 200.

The following examples further illustrate the present invention.

In the examples, various linear esters were prepared from carbon monoxide and the appropriate alkene using methanol as the source of hydroxyl groups.

All experiments were carried out in a vacuum-argon Schlenk line using dried and degassed Schlenk glassware.

1-octene was dried over molecular sieves and degassed by bubbling with argon. 1-dodecene (Aldrich) was purified by distillation. Methanol and deuteriated methanol (Aldrich) were dried over molecular sieves. Toluene was distilled from sodium diphenyl ketyl. Anisole (Aldrich) was not dried, but it was degassed by bubbling argon through the syringe. 1,2-bis (di-tertbutylphosphino)xylene (Lucite International) was stored and handled in the glove box due to its air sensitive nature. Tris(dibenzylidene acetone) dipalladium ($Pd_2(dba)_3$). (Aldrich) was used as metal precursor and it can be weighed in air because it is stable.

Gas Chromatographic analyses were carried out on a Hewlett-Packard 5890 series gas chromatograph equipped with a flame ionisation detector for quantitive analyses and a Hewlett-Packard 5890 series mass selective detector for qualitative analyses.

When the substrate was butadiene the solution preparation was different. As butadiene is a volatile liquid it is more difficult to manipulate. It was condensed into a graduated Schlenk tube cooled in liquid nitrogen and then transferred to an autoclave cooled in an acetone-dry ice bath.

The catalytic solutions containing toluene were prepared in a dried and degassed Schlenk tube and then transferred to the autoclave.

The catalytic solutions were made up as follows $Pd_2 (dba)_3$ and 1,2-bis (di-tert-butyl phosphino) xylene were added to a Schlenk tube in a glove box. Methanol (typically 10 cm$^3$) was then added with a syringe and the solution was warmed with a heat gun to dissolve all the solids. Once the tube was cooled, the substrate for carbonylation (2 cm$^3$) and methane sulphonic acid (MSA) were added. The experiments were carried out under various partial pressures of carbon monoxide and at various temperatures in a dried and degassed flask. Then the carbon monoxide was typically bubbled through the solution with a needle. Where, as in most cases, the reaction was carried out without toluene using only methanol as the solvent, the phosphine ligand was added after the catalytic solution because it is insoluble in the solvent. However, the phosphine ligand can be dissolved in methanol when the solution is warmed.

The autoclaves used were made of stainless steel or hastelloy. They were cleaned successively with acid, water and acetone and dried in an oven. Inside them, a glass liner was introduced with a magnetic stirrer. The whole system was flushed three times with carbon monoxide and then taken to the appropriate pressure. The system was then held at the reaction temperature for between 3 and 10 hours and then cooled in air. The yellow solution obtained was analysed by GC-MS.

The experiments conducted are shown in Tables 1 and 2. The amounts of palladium compound, ligand, MSA and substrate are expressed in mmoles. The solvent is given in ml. RT stands for room temperature ie. 20° C. The percentage conversion is an expression of the amount of substrate converted by the reaction whereas the selectivity is a measure of the selectivity to linear carbonylated product. l:b is a representation of the linear:branched ratio of such carbonylated products.

The total volume is the volume of MeOH+the volume of substrate (unless otherwise stated). The palladium source is Pd$_2$(dba). Examples 1 and 2 used 4×10$^5$ moles Pd, a 3:1 ratio of ligand:Pd and a 10:1 ratio of acid:palladium. In examples 3, 4 and 5 45.7 mg of Pd(dba) was used. Example 3 utilised a 10:1 ligand:palladium ratio. Examples 4 and 5 were carried out at a 5:1 ligand:palladium ratio. Example 6 used 4×10$^{-5}$ moles Pd, a 3:1 ratio of ligand:Pd and a 6.3:1 ratio of acid:palladium. Examples 7-10 were carried out with 73.7 mg of Pd(dba) with ligand:palladium of 3:1 and acid:palladium of 10:1. Examples 11-26 were carried out with 45.7 mg of Pd(dba), a 5:1 ligand:palladium ratio and a 10:1 acid:palladium ratio. The substrate is shown in mmoles The balance of volume is made up by the methanol solvent. The substrate and temperatures are varied.

show an improvement at such temperatures. A similar series of experiments was carried out in examples 14-16 with respect to 1 dodecene and relating to temperatures of room temperature, 10 and 0° C. respectively. Again, excellent selectivity was found at all three temperatures whereas the highest linear:branched ratio is found at 0° C. The same set of experiments carried out with respect to 1-hexene in example 17-19 shows full conversion within 3 hours as well as 100% selectivity and greater than 100:1 linear:branched ratio. Unsurprisingly, the increase in chain length from hexene to dodecene results in a lower reaction rate and may possibly be due to the steric hindrance provided by the phosphine ligand but this does not affect the efficacy of the process.

Example 20 shows that even 1-octadecene has 100% selectivity and greater than a 100 ratio of linear:branched product at room temperature. Examples 21-26 show linear (carbonylation of the 1-alkene) results fore branched alkenes and with the exception of example 24 show good selectivity. Example 24 is a variation on example 21 in that the carbon monoxide is passed over the solution rather than bubbled through solution. In this scenario, it appears that the starting

TABLE 1

| Example | [Pd] mmol | [L] mmol | [MSA] mmol | Solvent | Substrate | Total Vol (ml) | Subs vol (ml) | T(h) | T(C) | P(bar) | % conv | l:b | select (%) | Product |
|---|---|---|---|---|---|---|---|---|---|---|---|---|---|---|
| 1 Comp | 0.04 | 0.12 | 0.4 | MeOH | 1-octene | 8 | 2 | 6.5 | 100 | 30 | 95.8 | 13.3:1 | 93.0 | Methyl nonanoate |
| 2 Comp | 0.04 | 0.12 | 0.4 | MeOH | 1-octene | 8 | 2 | 7.0 | 100 | 30 | 97.7 | 13.0:1 | 92.9 | Methyl nonanoate |
| 3 Comp | 0.1 | 1.0 | 1.0 | Tol (9 ml) + MeOH (2 ml) | 1-octene | 13 | 2 | 3 | 80 | 30 | 85.3 | 28:1 | 96.3 | Methyl nonanoate |
| 4 Comp | 0.1 | 0.500 | 1.0 | MeOH | 1-octene | 12 | 2 | 3 | 80 | 30 | 93.4 | 15:1 | 93.4 | Methyl nonanoate |
| 5 Comp | 0.1 | 0.500 | 1.0 | Anis (4 ml) + MeOH | 1-octene | 12 | 2 | 3 | 80 | 30 | 95.5 | >99:1 | 98.0 | Methyl nonanoate |
| 6 | 0.04 | 0.12 | 0.25 | MeOH | 1-octene | 12 | 2 | 10 | 40 | 10 | 96.1 | 23:1 | 95.9 | Methyl nonanoate |
| 7 | 0.1 | 0.5 | 1.0 | MeOH | 1-octene | 12 | 2 | 3 | RT | 1 | 97.8 | >99.5:1 | 100 | Methyl nonanoate |
| 8 | 0.16 | 0.48 | 1.0 | MeOH | 2-octene | 26 | 2 | 3 | RT | 1 | 29.2 | >99.5:1 | 100.0 | Methyl nonanoate |
| 9 | 0.16 | 0.48 | 1.0 | MeOH | 1-dodecene | 26 | 2 | 4.5 | RT | 1 | 37.3 | >99:1 | 100.0 | Methyl tridecanoate |
| 10 | 0.1 | 0.5 | 1.0 | MeOH | 1-octene | 12 | 2 | 3 | RT | 30 | 50% | 56.8:1 | 98.5 | Methyl nonanoate |

Comparative examples 1-5 show the effect of carrying out the reaction at a relatively high temperature and 30 bar pressure. Selectivity is generally at moderate levels, in comparitive example 5 when anisole is introduced as the aprotic solvent. However, as shown by example 7, an improved selectivity and linear:branched ratio is obtained when the reaction is carried out at room temperature and 1 bar pressure without the use of an added aprotic solvent. Furthermore, as shown by example 8, a similarly high selectivity and linear:branched ratio is obtained with 2-octene, although the rate of reaction is slower which accounts for the low percentage conversion after 3 hours of 29.2. A similar situation applies with respect to example 9 which relates to 1-dodecene. Example 10 constitutes a repeat of example 7 except that the pressure is raised to 30 bar. It should be noted that this has the effect of lowering the reaction rate to 50% conversion after 3 hours and also significantly lowering the linear:branched ratio.

Table 2 shows further examples 11-26. Examples 11-13 relate to the same experiment carried out in relation to 1-octene but at variable temperatures of 0, 10 and −30° C. From these experiments, it can readily be seen that lowering the temperature of reaction decreases the reaction rate and, accordingly, lowers the percentage conversion after 3 hours. However, selectivity and linear:branched ratio continues to substrate has sufficient time to isomerise prior to carbonylation, presumably due to the lower rate of exposure to carbon monoxide. The pressure of the process is shown as total pressure in tables 1 & 2 but this is equivalent to the CO pressure.

Accordingly, the results show that contrary to prior art teaching, it is not necessary to carry out carbonylation by increasing temperature or carbon monoxide partial pressure. In fact, the examples illustrate that poor selectivity and poor linear:branching ratios are found at increased temperatures and pressures and that surprisingly better selectivity and linear:branched ratios are found in the temperature and pressure ranges of the invention.

By linear carbonylation is meant carbonylation at the 1-alkene giving the carbonyl group alpha to the C$_1$ carbon atom and not necessarily the absence of branched product, where the starting material is itself branched.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/ or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

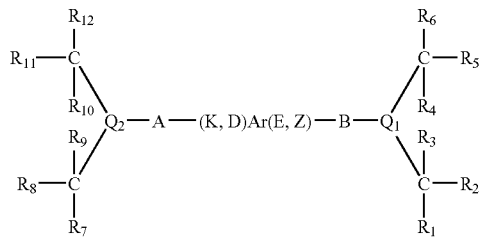

wherein:

Ar is a bridging group comprising an optionally substituted aryl moiety to which the phosphorus atoms are linked on available adjacent carbon atoms;

A and B each independently represent lower alkylene;

TABLE 2

| Example | [Pd] (mmol) | [L] (mmol) | {MSA} (mmol) | Solvent | Substrate | [subs] (ml) | Total vol (ml) | t (h) | P (bar) | T (C) | Conv (%) | Selec (%) | l:b | Product |
|---|---|---|---|---|---|---|---|---|---|---|---|---|---|---|
| 11 | 0.1 | 0.5 | 1.0 | MeOH | 1-octene | 2.0 | 12 | 3 | 1 | 0 | 28.9 | 99 | 98.6 | Methyl nonanoate |
| 12 | 0.1 | 0.5 | 1.0 | MeOH | 1-octene | 2.0 | 12 | 3 | 1 | 10 | 100 | 99 | 126 | Methyl nonanoate |
| 13 | 0.1 | 0.5 | 1.0 | MeOH | 1-octene | 2.0 | 12 | 3 | 1 | −30 | 1.27 | 100 | >100 | Methyl nonanoate |
| 14 | 0.1 | 0.5 | 1.0 | MeOH | 1-dodecene | 2.0 | 12 | 3 | 1 | RT | 30.3 | 98 | 55.2 | Methyl tridecanoate |
| 15 | 0.1 | 0.5 | 1.0 | MeOH | 1-dodecene | 2.0 | 12 | 3 | 1 | 10 | 26.6 | 99 | 89 | Methyl tridecanoate |
| 16 | 0.1 | 0.5 | 1.0 | MeOH | 1-dodecene | 2.0 | 12 | 3 | 1 | 0 | 18.2 | 99 | 91 | Methyl tridecanoate |
| 17 | 0.1 | 0.5 | 1.0 | MeOH | 1-hexene | 2.0 | 12 | 3 | 1 | RT | 100 | 100 | >100 | Methyl heptanoate |
| 18 | 0.1 | 0.5 | 1.0 | MeOH | 1-hexene | 2.0 | 12 | 3 | 1 | 10 | 100 | 100 | >100 | Methyl heptanoate |
| 19 | 0.1 | 0.5 | 1.0 | MeOH | 1-hexene | 2.0 | 12 | 3 | 1 | 0 | 100 | 100 | >100 | Methyl heptanoate |
| 20 | 0.1 | 0.5 | 1.0 | MeOH | 1-octadecene | 2.0 | 12 | 3 | 1 | RT | 5.7 | 100 | >100 | Methyl nonadecanoate |
| 21 | 0.1 | 0.5 | 1.0 | MeOH | 2-me-1-pentene (bubbled) | 1.20 | 11.2 | 3 | 1 | RT | 100 | 96 | 22 | Methyl-3-methyl hexanoate |
| 22 | 0.1 | 0.5 | 1.0 | MeOH | 3-me-1-pentene (bubbled) | 1.20 | 11.2 | 3 | 1 | RT | 100 | 100 | >100 | Methyl-4-methyl hexanoate |
| 23 | 0.1 | 0.5 | 1.0 | MeOH | 4-me-1-pentene (bubbled) | 1.20 | 11.2 | 3 | 1 | RT | 100 | 99.4 | 16.6 | Methyl-5-methyl hexanoate |
| 24 | 0.1 | 0.5 | 1.0 | MeOH | 2-me-1-pentene (passed over) | 1.20 | 11.2 | 3 | 1 | RT | 100 | 89 | 8.1 | Methyl-5-methyl hexanoate |
| 25 | 0.1 | 0.5 | 1.0 | MeOH | 2-me-2-pentene (bubbled) | 1.20 | 11.2 | 3 | 1 | RT | 100 | 97 | 32 | Methyl-5-methyl hexanoate |
| 26 | 0.1 | 0.5 | 1.0 | MeOH | 4-me-2-pentene (bubbled) | 1.20 | 11.2 | 3 | 1 | RT | 100 | 100 | >100 | Methyl-5-methyl hexanoate |

The invention claimed is:

1. A process for the carbonylation of $C_3$-$C_{20}$ ethylenically unsaturated compounds which process comprises reacting said $C_3$-$C_{20}$ ethylenically unsaturated compound with carbon monoxide in the presence of a source of hydroxyl groups and of a catalyst system, the catalyst system obtainable by combining:

(a) a metal of Group VIII or a compound thereof: and (b) a bidentate phosphine, stibine or arsine of general formula (I)

K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or -J-$Q^3(CR^{13}(R^{14})(R^{15}))CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$;

$R^1$ to $R^{18}$ each independently represent lower alkyl, aryl, or Het;

$R^{19}$ to $R^{27}$ each independently represent hydrogen, lower alkyl, aryl or Het;

each of $Q^1$, $Q^2$ and $Q^3$ is independently selected from the group consisting of phosphorous, arsenic or antimony;

wherein the carbonylation reaction is carried out at a temperature of between $-30°$ C. to $49°$ C. and under a CO partial pressure of less than $30 \times 10^5$ N.m$^{-2}$.

2. A process according to claim 1, wherein $R^1$ to $R^{18}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein).

3. A process according to claim 1, wherein $R^1$ to $R^{18}$ each independently represent non-substituted $C_1$ to $C_6$ alkyl.

4. A process according to claim 1, wherein each of the groups $R^1$ to $R^3$, $R^4$ to $R^6$, $R^7$ to $R^9$, $R^{10}$ to $R^{12}$, $R^{13}$ to $R^{15}$ or $R^{16}$ to $R^{18}$ together independently may form cyclic structures.

5. A process according to claim 1, wherein each $R^1$ to $R^{18}$ group represents the same lower alkyl, aryl, or Het moiety as defined herein.

6. A process according to claim 1, wherein, each $R^1$ to $R^{18}$ represents methyl.

7. A process according to claim 1, wherein each $Q^1$, $Q^2$ and $Q^3$ (when present) represents phosphorous.

8. A process according to claim 1, wherein in the compound of formula I, A, B and J (when present) each independently represent $C_1$ to $C_6$ alkylene which is optionally substituted as defined herein.

9. A process according to claim 1, wherein the lower alkylene which A, B and J may independently represent is —$CH_2$— or —$C_2H_4$—.

10. A process according to claim 1, wherein K, D, E or Z independently represents hydrogen.

11. A process according to claim 1, wherein two of K, D, E and Z together with the carbon atoms of the aryl ring to which they are attached form a phenyl ring, the phenyl ring being optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)RN^{25}R^{26}$, wherein $R^9$ to $R^{27}$ each independently represent hydrogen or lower alkyl (which alkyl group may itself be optionally substituted or terminated as defined herein).

12. A process according to claim 1, wherein the hydroxyl group containing compound includes water or an organic molecule having a hydroxyl functional group.

13. A process according to claim 12, wherein, the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)RN^{25}R^{26}$, $SR^{27}$ or $C(O)SR^{27}$ as defined herein. Highly preferred alkanols are $C_1$-$C_8$ alikanols such as methanol, ethanol, propanol, iso-propanol, iso-butanol, t-butyl alcohol, n-butanol, phenol and chlorocapryl alcohol.

14. A process according to claim 1, wherein the carbonylation of an ethylenically unsaturated compound as defined herein may be performed in one or more aprotic solvents.

15. A process according to claim 1, wherein the reaction is carried out in the absence of any external aprotic solvent ie. an aprotic solvent not generated by the reaction itself.

16. A process according to claim 1, wherein the process is carried out with the catalyst comprising a support.

17. A process according to claim 15, wherein the support material is porous silica which has a surface area in the range of from 10 to 700 m$^2$/g, a total pore volume in the range of from 0.1 to 4.0 cc/g and an average particle size in the range of from 10 to 50 μm.

18. A process according to claim 1, wherein the organic groups $R^1$, $R^2$, $R^3$, $R^4$, $R^5$, $R^6$, $R^7$, $R^8$, $R^9$, $R^{10}$, $R^{11}$ and $R^{12}$ when associated with their respective carbon atom form composite groups which are at least as sterically hindering as t-butyl.

19. A process according to claim 1, wherein the bidentate ligands are selected from bis(di-t-butyl phosphino)-o-xylene (also known as 1,2bis (di-t-butylphosphinomethyl)benzene); 1,2bis(diadamantyiphosphinomethyl) benzene; 1,2bis(di-adamantyiphosphinomethyl)naphthalene; 1,2bis(di-t-pentyl phosphino)-o-xylene (also known as 1,2bis(di-t-pentyl-phosphinomethyl)beuzene); and bis 1,2(di-t-butyl phosphino)naphthalene.

20. A process according to claim 1 wherein suitable Group VIIIB metals or a compound thereof which may be combined with a compound of formula I include cobalt, nickel, palladium, rhodium and platinum.

21. A process according to claim 19, wherein suitable compounds of such Group VIII metals include: salts of such metals with, or compounds comprising weakly coordinated anions derived from, nitric acid; sulphuric acid; lower alkanoic (up to $C_{12}$) acids; sulphonic acids; sulphonated ion exchange resins; perhalic acid; halogenated carboxylic acids; orthophosphoric acid; phosphonic acids; and acids derived from interactions between Lewis acids and Broensted acids; the optionally halogenated tetraphenyl borate derivatives; zerovalent palladium.

22. A process according to claim 21, wherein the anion may be derived from or introduced as one or more of an acid having a pKa measured in aqueous solution at $18°$ C. of less than 4.

23. A process according to claim 1, wherein the carbonylation is carried out at a temperature of between $-10$ to $45°$ C.

24. A process according to claim 1, wherein the carbonylation is carried out at a CO partial pressure of less than $15 \times 10^5$ N.m$^{-2}$.

25. A process according to claim 1, wherein the reaction is carried out on ethylenically unsaturated $C_3$-$C_{20}$ compounds.

26. A process according to claim 1, wherein the ethylenically unsaturated compound is an alkene having 1, 2, 3 or more carbon-carbon double bonds per molecule.

27. A process according to claim 1, wherein the ethylenically unsaturated compound may, when there are sufficient number of carbon atoms, be linear or branched, be substituted, be cyclic, acyclic or part cyclic/acyclic, and/or be optionally substituted or terminated by one or more substituents selected from lower alkyl, aryl, alkylaryl, Het, alkylHet, halo, $OR^{19}$, $OC(O)R^{20}$, $C(O)R^{21}$, $C(O)OR^{22}$, $NR^{23}R^{24}$, $C(O)NR^{25}R^{26}$, $NO_2$, CN, $SR^{27}$ wherein $R^{19}$ to $R^{27}$ each independently represent hydrogen or lower alkyl.

28. A process according to claim 1, wherein the ethylenically unsaturated compounds may be independently selected from ethene, propene, 1-butene, 2-butene, isobutene, 1-pentene, 2-pentene, 3-pentene and branched isomers thereof, 1-hexene and its isomers, 1-heptene and its isomers, 1-octene and its isomers, 1-nonene and its isomers, 1-decene and its isomers, the $C_{11}$-$C_{20}$ alkenes and their known isomers, 3-pentenenitrile, methyl-3-penteneoate, 1,3 butadiene, 1,3-pentadiene, 1,3 hexadiene, 1,3 cyclohexadiene, 2,4-leptadiene, 2-methyl 1,3 butadiene.

29. A process according to claim 1, wherein $R^1$ to $R^{18}$ each independently is selected from the group consisting of methyl, ethyl, n-propyl, iso-propyl, n-butyl, iso-butyl, tert-butyl, pentyl, hexyl and cyclohexyl.

30. A process according to claim 1, wherein each of said cyclic structures is selected from the group consisting of adamantyl, 1-norbomyl or 1-norbomadienyl.

31. A process according to claim 19, wherein each of said weakly coordinated anions is derived from an acid selected from the group consisting of acetic acid, propionic acid; methane suiphonic acid, chlorosulphonic acid, fluorosulphonic acid, trifluoromethane suiphonic acid, benzene sulphonic acid, naphthalene sulphonic acid, toluene sulphonic acid, p-toluene suiphonic acid, t-butyl suiphonic acid, and 2-hydroxypropane sulphomc acid; suiphonated ion exchange resins; perchioric acid; trichloroacetic acid; trifluoroacetic acid; orthophosphoric acid; and benzenephosphonic acid.

32. A process according to claim 12, wherein, the organic molecule having a hydroxyl functional group is a $C_1$-$C_8$ alkanols selected from the group consisting of methanol, ethanol, propanol, iso-propanol, iso-butanol, t-butyl alcohol, n-butanol, phenol and chlorocapryl alcohol.

33. A process according to claim 21, wherein the palladium complex is tri(dibenzylideneacetone)di-palladium.

* * * * *